United States Patent [19]
Rogers

[11] Patent Number: 5,738,144
[45] Date of Patent: Apr. 14, 1998

[54] LUER CONNECTING COUPLING

[75] Inventor: Russell L. Rogers, Munith, Mich.

[73] Assignee: Aeroquip Corporation, Maumee, Ohio

[21] Appl. No.: 729,402

[22] Filed: Oct. 11, 1996

[51] Int. Cl.⁶ ................................... F16L 37/28
[52] U.S. Cl. ................ 137/614.03; 251/149.1; 251/149.4; 251/149.6
[58] Field of Search ............... 137/614.03; 251/149.4, 251/149.6, 149.1

[56] References Cited

U.S. PATENT DOCUMENTS

| | | | |
|---|---|---|---|
| 4,002,186 | 1/1977 | Fink et al. | 137/614.03 |
| 4,949,745 | 8/1990 | McKeon | 137/614.03 |
| 4,991,627 | 2/1991 | Nix | 137/614.03 |
| 5,215,538 | 6/1993 | Larkin | 251/149.1 |
| 5,358,001 | 10/1994 | Smith | 251/149.1 |
| 5,405,323 | 4/1995 | Rogers et al. | |

*Primary Examiner*—A. Michael Chambers
*Attorney, Agent, or Firm*—Jones, Day, Reavis & Pogue

[57] ABSTRACT

A luer connecting coupling including a first body member, a resilient seal, a second body member, a tubular valve and a reciprocating valve sleeve. The first body member defines a passageway. The resilient seal is positioned in the passageway. The second body member defines a chamber. The tubular valve is positioned in the chamber. The tubular valve defines at least one fluid opening. The reciprocating valve sleeve is in communication with the tubular valve. The sleeve is movable between a first position and a second position to close or open the fluid opening of the tubular valve. When the coupling is disconnected, the components are self-sealing.

18 Claims, 5 Drawing Sheets

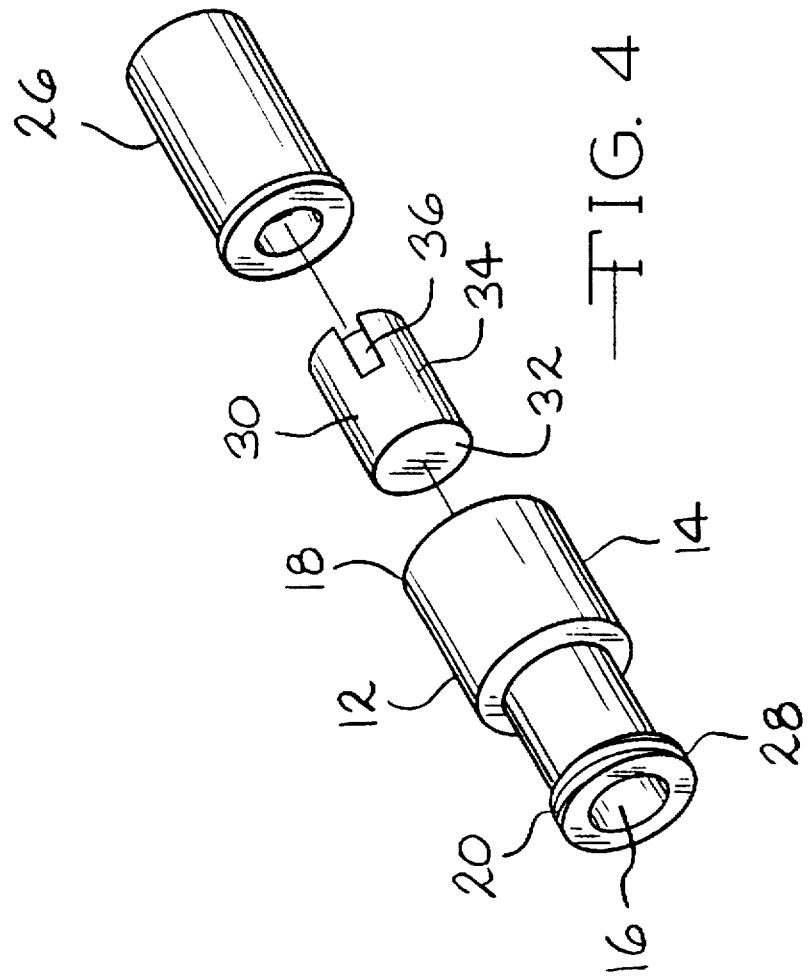

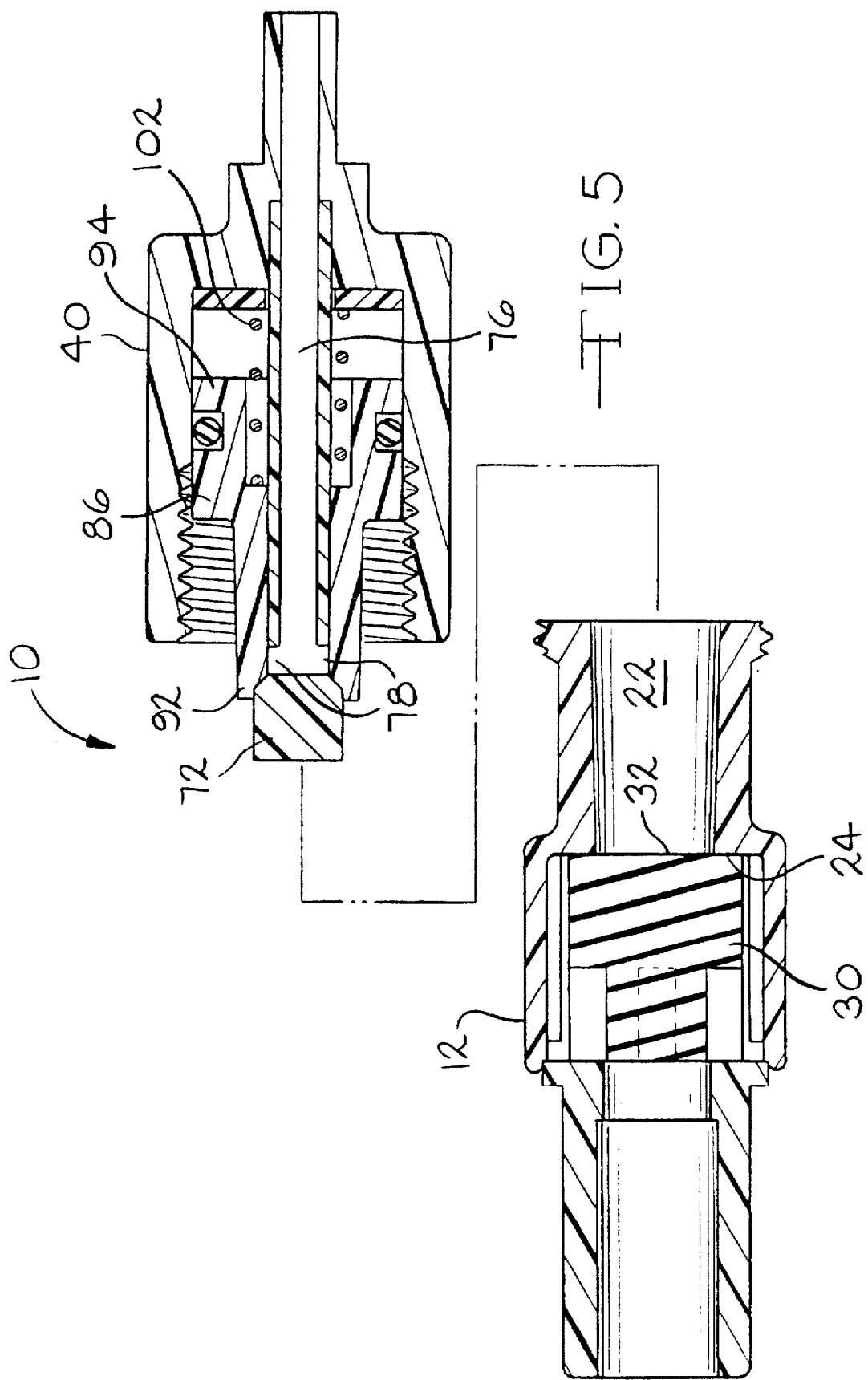

5,738,144

LUER CONNECTING COUPLING

BACKGROUND OF THE INVENTION

The present invention relates to a luer connecting coupling. More specifically, the invention is directed to a coupling having two body members that both include fluid sealing devices.

Luer lock fittings are known in the art. These fittings are used, for example, to connect tubing from an intravenous (IV) bag to tubing leading to a catheter that has been inserted in the blood vessel of a patient. It has been found that when the coupling members of the prior art connectors are disconnected they allow for the escape of fluid.

There is a need for a luer connecting coupling that includes self-sealing valves on both coupling members to prevent the escape of fluid when the coupling members are disconnected. The present invention satisfies this need.

SUMMARY OF THE INVENTION

The luer connecting coupling of the present invention includes a first body member having an exterior surface and an interior surface. The interior surface defines a passageway having a shoulder. A resilient seal is positioned in the passageway adjacent the shoulder for sealing the passageway.

The coupling further includes a second body member having an outer surface and an inner surface. The inner surface defines a chamber.

A tubular valve having a seal end and a body end is positioned in the chamber of the second body member. The valve includes a channel extending between the seal end and the body end. The valve defines at least one fluid opening in communication with the channel adjacent the seal end. The seal end is in communication with the resilient seal to unseat or seat the resilient seal.

A reciprocating valve sleeve is in communication with the tubular valve. The sleeve is movable between a first position and a second position to close or open the fluid opening of the valve.

It is the primary object of the present invention to provide a luer connecting coupling that provides self-sealing valves for each coupling member to prevent the escape of fluid when the members are disconnected.

Other objects and advantages of the present invention shall become apparent to those skilled in the art upon a review of the following detailed description of the preferred embodiment and the accompanying drawings.

BRIEF DESCRIPTION OF THE DRAWINGS

FIG. 4 is an exploded perspective view of the first body member, resilient seal and adapter according to the present invention; and FIG. 5 is a cross-sectional view similar to the view of FIG. 2 showing the disconnected coupling members according to the present invention.

DETAILED DESCRIPTION OF THE PREFERRED EMBODIMENT

Figure 1:
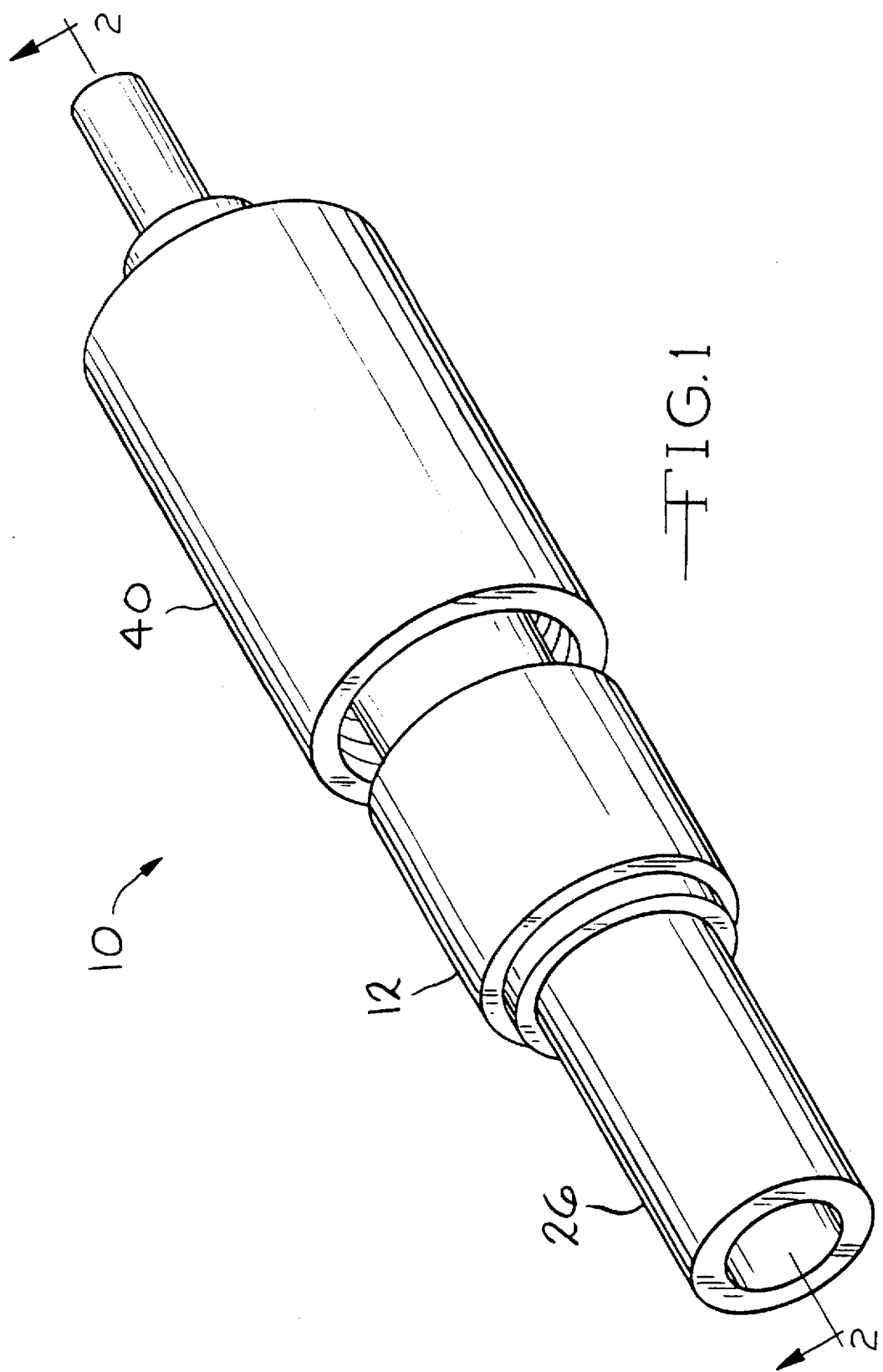
FIG. 1 is a perspective view of an embodiment of the luer connecting coupling according to the present invention.

The preferred embodiment and best mode of the present invention will now be described in detail with reference being made to the drawings. The luer connecting coupling of the present invention is indicated in the drawings by the reference number "10".

Figure 2:
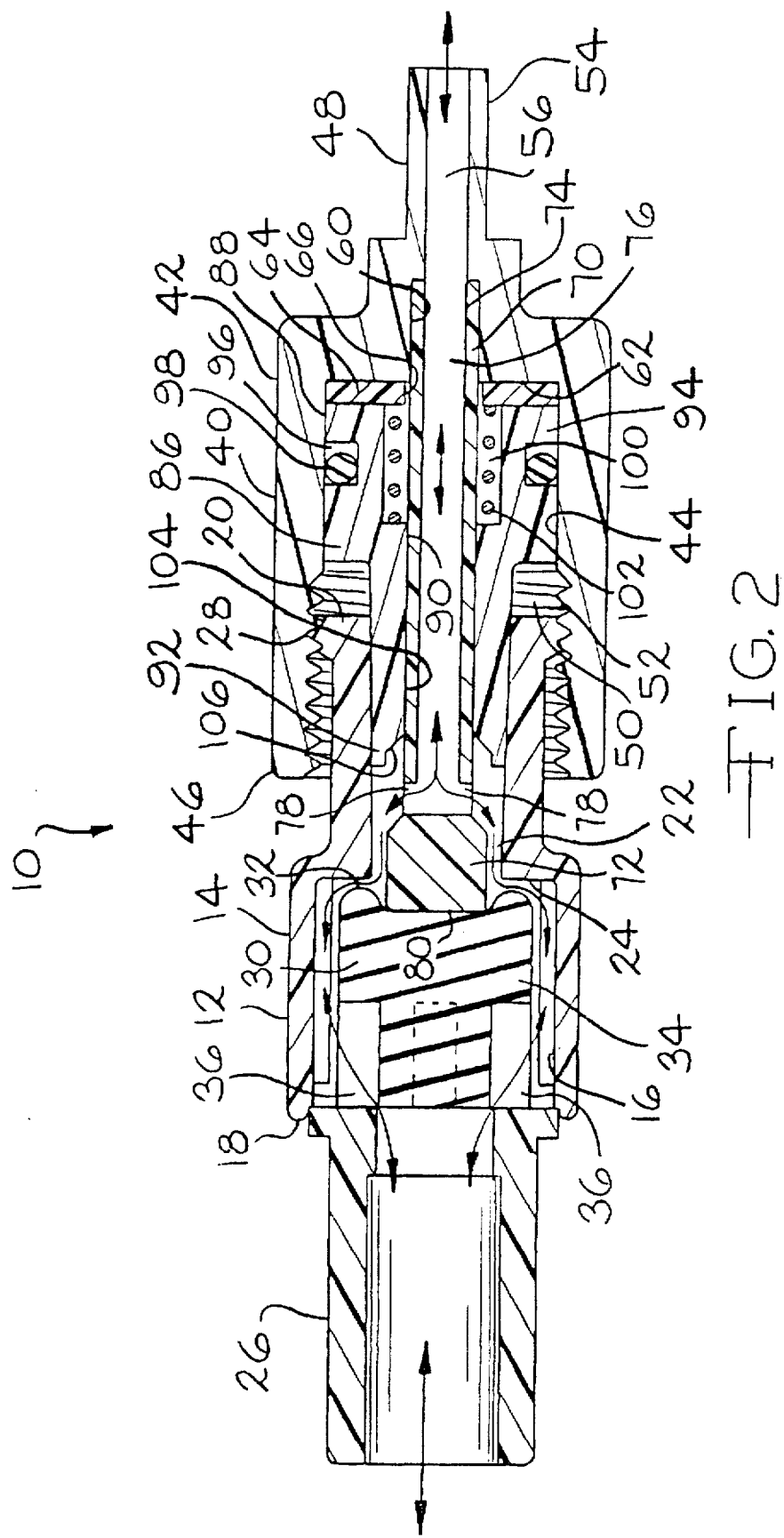
FIG. 2 is a cross-sectional view taken through lines 2—2 of FIG. 1.

Referring to FIGS. 1, 2 and 4, the coupling 10 includes a first body member 12 having an exterior surface 14, an interior surface 16, a first end 18 and a second end 20. The interior surface 16 defines a passageway 22 that extends longitudinally between the first end 18 and the second end 20. As shown in FIG. 2, the interior surface 16 defines an annular shoulder 24.

Referring to FIGS. 2 and 4, the coupling 10 includes an adapter 26 positioned at the first end 18 of the first body member 12. The adapter 26 can receive, for example, tubing leading to a catheter (not shown). It should be understood that the adapter 26 or the first end 18 can be attached to other types of tubing or devices depending on the application.

Still referring to FIGS. 2 and 4, the second end 20 of the first body member 12 includes a plurality of threads 28. As described below, the threads 28 are used to connect the coupling 10. The second end 20 and the threads 28 are usually constructed to conform with American National Standard Institute No. ANSI/HIMA MD70.1—1983 relating to luer lock fittings, which is incorporated herein by reference.

As shown in FIGS. 2 and 4, the coupling 10 includes a resilient seal 30 positioned in the passageway 22. The seal 30 includes a shoulder surface 32 that engages the shoulder 24. The resilient seal 30 further includes an annular wall 34 that corresponds to the interior surface 16 of the first body member 12. As shown in FIG. 4, the annular wall 34 defines at least one fluid recess 36. In the present embodiment, the annular wall 34 defines two opposed fluid recesses 36. The resilient seal can be comprised of a number of materials, with natural or synthetic rubber being preferred.

Figure 3:
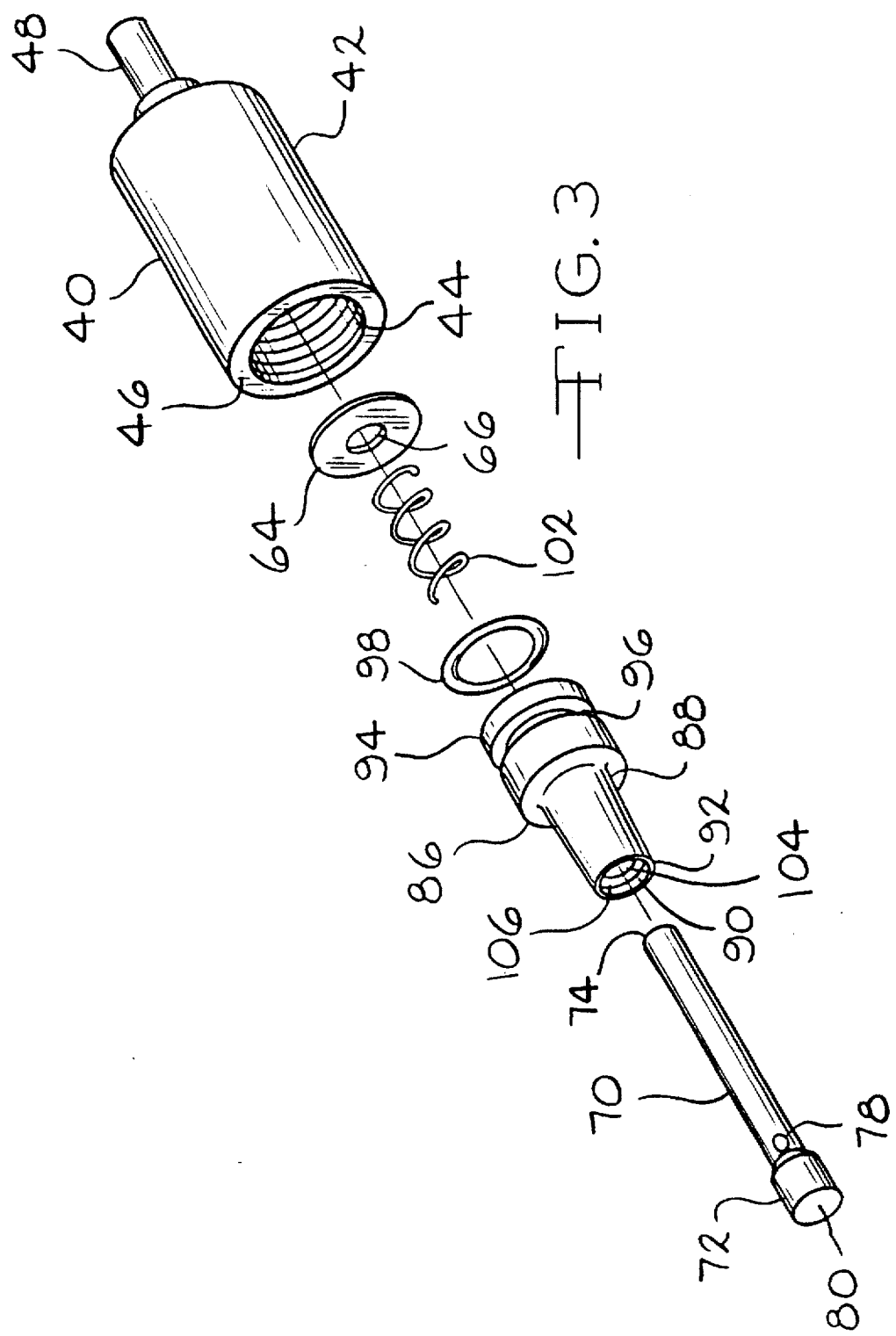
FIG. 3 is an exploded perspective view of the second body member, tubular valve and reciprocating valve sleeve according to the present invention.

Referring to FIGS. 1, 2 and 3, the coupling 10 includes a second body member 40 having an outer surface 42, an inner surface 44, a proximal end 46 and a distal end 48. As shown in FIG. 2, the inner surface 44 of the second body member 40 defines a chamber 50.

As shown in FIG. 2, the inner surface 44 of the second body member 40 defines threads 52 adjacent the proximal end 46. The threads 52 mate with the threads 28 of the first body member 12 to connect the respective body members.

As shown in FIG. 2, the distal end 48 of the second body member 40 includes a narrow projection 54 which is sized to receive, for example, IV tubing in communication with a bag containing fluid (not shown). It should be understood however that the distal end 48 can be connected to a variety of tubing or other devices depending on the application. A second passageway 56 is defined by the inner surface 44 of the second body member 40 adjacent the distal end 48. The second passageway 56 allows for the flow of fluid through the distal end 48.

Referring to FIGS. 2 and 3, the inner surface 44 of the second body member 40 defines a valve recess 60 adjacent the distal end 48. Further, the inner surface 44 defines a sleeve shoulder 62 adjacent the distal end 48. A spacer 64 having an opening 66 is positioned adjacent the sleeve shoulder 62.

Still referring to FIGS. 2 and 3, the coupling 10 includes a tubular valve 70 positioned in the chamber 50 of the second body member 40. The tubular valve 70 has a seal end 72 and a body end 74. The tubular valve 70 includes a channel 76 that extends longitudinally between the seal end 72 and the body end 74. The tubular valve 70 defines at least one fluid opening 78 in communication with the channel 76 adjacent the seal end 72. In the present embodiment, the tubular valve 70 defines two opposed fluid openings 78. As shown in FIG. 2, the seal end 72 includes a flat seal surface 80.

Referring to FIG. 2, the body end 74 of the tubular valve 70 is received by the valve recess 60 defined by the second body member 40. The body end 74 can either be fixedly attached or snugly engaged in the valve recess 60 to properly maintain the tubular valve 70 in the chamber 50.

Referring to FIGS. 2 and 3, the coupling 10 includes a valve sleeve 86 having an outside surface 88, an inside surface 90, a channel end 92 and a spring end 94. The outside surface 88 defines an O-ring recess 96 adjacent the spring end 94. An O-ring 98 is positioned in the O-ring recess 96 to provide a seal between the inner surface 44 of the second body member 40 and the outside surface 88 of the valve sleeve 86.

Still referring to FIGS. 2 and 3, the outside surface 88 of the valve sleeve 86 is angled or tapered at the channel end 92. As described below, this allows for the valve sleeve 86 to be moved from the proximal end 46 toward the distal end 48 of the second body member 40 during connection of the first and second body members 12 and 40.

As shown in FIG. 2, the inside surface 90 of the valve sleeve 86 defines a spring cavity 100 adjacent the spring end 94. A spring 102 is positioned in the spring cavity 100. A variety of springs can be used, with a coiled spring that surrounds the tubular valve 70 being preferred. When the coupling 10 is connected, as shown in FIG. 2, the spring 100 engages the spacer 64.

Referring to FIGS. 2 and 3, the inside surface 90 of the valve sleeve 86 defines a tubular valve cavity 104 that extends longitudinally between the channel end 92 and the spring end 94. The tubular valve 70 is positioned in the tubular valve cavity 104. As shown in FIG. 2, the inside surface 90 of the valve sleeve 86 defines a shape 106 corresponding to the shape of the seal end 72 of the tubular valve 70. In the preferred embodiment, the shape 106 is defined adjacent the channel end 92. As described below, the shape 106 provides for a tight seal of the fluid openings 78 by the inside surface 90 of the valve sleeve 86.

The valve sleeve 86 is movable from a first position adjacent the seal end 72 of the tubular valve 70 to a second position spaced from the seal end. When the channel end 92 of the valve sleeve 86 is positioned adjacent the seal end 72 of the tubular valve 70, the inside surface 90 closes the fluid openings 78. When the channel end 92 is spaced from the seal end 72, as shown in FIG. 2, the fluid openings 78 are open.

The operation of the coupling 10 will now be described. Referring to FIG. 5, the first body member 12 is shown disconnected from the second body member 40. When the members are disconnected, the shoulder surface 32 of the resilient seal 30 is seated against the shoulder 24 of the first body member 12. This seal prevents the flow of fluid in either direction through the passageway 22 of the first body member 12. When the second body member 40 is disconnected, the spring 102 forces the channel end 92 of the valve sleeve 86 having the shape 106 against the seal end 72 of the tubular valve 70 to close or seal the fluid openings 78 defined by the tubular valve. This seal prevents the flow of fluid through the channel 76 of the tubular valve 70. Thus, the seals created in the first and second body members 12 and 40 prevent the escape of fluid from the members when the coupling 10 is disconnected.

Referring to FIG. 2, the first body member 12 is connected to the second body member 40 by turning the members to cause the threads 28 and the threads 52 to mate. As the members are being threaded together, the seal surface 80 of the seal end 72 engages the shoulder surface 32 of the seal 30 to cause the seal to become unseated from the shoulder 24. The breaking of the seal between the resilient seal 30 and the shoulder 24 allows for the flow of fluid in the directions indicated by the arrows in FIG. 2.

As the first and second body members 12 and 40 are being threaded together, the tapered channel end 92 of the valve sleeve 86 engages the interior surface 16 of the first body member 12. This engagement causes a wedging action that forces the valve sleeve 86 to move from the first position as shown in FIG. 5 to the second position as shown in FIG. 2. In the second position, the channel end 92 of the valve sleeve 86 is spaced from the seal end 72 of the tubular valve 70 so that the fluid openings 78 are open. This allows for the flow of fluid in the directions indicated by the arrows in FIG. 2.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

I claim:

1. A luer body member having an exterior surface and an interior surface, said interior surface defining a passageway having a shoulder;

a resilient seal positioned in said passageway adjacent said shoulder for sealing said passageway;

a second body member having an outer surface and an inner surface, said inner surface defining a chamber;

a tubular valve having a seal end and a body end positioned in said chamber, said valve including a channel extending between said seal end and said body end, said valve defining at least one fluid opening in communication with said channel adjacent said seal end, said seal end being in communication with said resilient seal to respectively unseat and seat said resilient seal with respect to said shoulder; and a valve sleeve in communication with said tubular valve, said sleeve being movable between a first position and a second position to respectively close and open said fluid opening of said valve.

2. The coupling of claim 1, wherein said first body member further includes a first end, said coupling including an adapter for receiving tubing positioned at said first end.

3. The coupling of claim 1, wherein said first body member further includes a second end, said second end including threads.

4. The coupling of claim 1, wherein said resilient seal includes a shoulder surface for engaging said shoulder.

5. The coupling of claim 1, wherein said resilient seal includes an annular wall defining at least one fluid recess.

6. The coupling of claim 1, wherein said resilient seal is comprised of rubber.

7. The coupling of claim 1, wherein said second body member includes a proximal end and a distal end.

8. The coupling of claim 7, wherein said proximal end includes threads.

9. The coupling of claim 7, wherein said distal end is adapted to receive tubing.

10. The coupling of claim 7, wherein said inner surface adjacent said distal end defines a second passageway in communication with said channel.

11. The coupling of claim 7, wherein said inner surface adjacent said distal end defines a valve recess for receiving said body end of said tubular valve.

12. The coupling of claim 7, wherein said inner surface adjacent said distal end defines a sleeve shoulder in communication with said valve sleeve.

13. The coupling of claim 1, wherein said valve sleeve includes an outside surface, an inside surface, a channel end and a spring end.

14. The coupling of claim 13, wherein said outside surface defines an O-ring recess adjacent said spring end, an O-ring positioned in said O-ring recess.

15. The coupling of claim 13, wherein said outside surface is tapered at said channel end.

16. The coupling of claim 13, wherein said inside surface defines a spring cavity adjacent said spring end, a spring positioned in said spring cavity.

17. The coupling of claim 13, wherein said inside surface defines a tubular valve cavity for receiving said tubular valve.

18. The coupling of claim 13, wherein said inside surface defines a shape corresponding to said seal end of said tubular valve adjacent said channel end.

* * * * *